United States Patent
Mayer et al.

(10) Patent No.: US 7,624,622 B1
(45) Date of Patent: Dec. 1, 2009

(54) METHOD OF MEASURING THE TRANSMISSION RATE OF A PERMEANT THROUGH A CONTAINER AND DETERMINING SHELF LIFE OF A PACKAGED PRODUCT WITHIN THE CONTAINER

(75) Inventors: Daniel W. Mayer, Wyoming, MN (US); Stephen D. Tuomela, Ramsey, MN (US)

(73) Assignee: Mocon, Inc., Minneapolis, MN (US)

( * ) Notice: Subject to any disclaimer, the term of this patent is extended or adjusted under 35 U.S.C. 154(b) by 53 days.

(21) Appl. No.: 11/753,181

(22) Filed: May 24, 2007

Related U.S. Application Data

(60) Provisional application No. 60/808,706, filed on May 26, 2006.

(51) Int. Cl.
 *G01N 15/08* (2006.01)
(52) U.S. Cl. .......................................... 73/38
(58) Field of Classification Search ............... 73/38, 73/40, 40.7, 49.2, 49.3, 49.8
 See application file for complete search history.

(56) References Cited

U.S. PATENT DOCUMENTS

| 3,081,250 | A | | 3/1963 | Hall et al. | |
|---|---|---|---|---|---|
| 3,337,441 | A | | 8/1967 | Goldsmith | |
| 4,047,422 | A | * | 9/1977 | Lyssy | 73/38 |
| 4,800,000 | A | | 1/1989 | Zatko et al. | |
| 5,513,515 | A | | 5/1996 | Mayer | |
| 5,591,898 | A | | 1/1997 | Mayer | |
| 6,018,987 | A | | 2/2000 | Mayer et al. | |
| 6,354,138 | B1 | | 3/2002 | Ascheman et al. | |
| 6,640,615 | B1 | * | 11/2003 | Morrow | 73/38 |
| 6,857,307 | B2 | * | 2/2005 | Gebele et al. | 73/38 |
| 6,892,567 | B1 | * | 5/2005 | Morrow | 73/38 |
| 6,964,191 | B1 | * | 11/2005 | Tata | 73/38 |
| 7,278,292 | B2 | * | 10/2007 | Wild et al. | 73/38 |
| 2002/0194899 | A1 | * | 12/2002 | Gebele et al. | 73/38 |
| 2004/0040372 | A1 | * | 3/2004 | Plester et al. | 73/38 |
| 2006/0032293 | A1 | * | 2/2006 | Wild et al. | 73/38 |

FOREIGN PATENT DOCUMENTS

| DE | 19642009 C2 | 4/1997 |
|---|---|---|
| EP | 326421 A | 8/1989 |
| GB | 2008772 A | 6/1979 |
| GB | 2306223 A | 4/1997 |

* cited by examiner

*Primary Examiner*—John Fitzgerald
(74) *Attorney, Agent, or Firm*—Sherrill Law Offices, PLLC

(57) ABSTRACT

A method of measuring the transmission rate of a permeant through a container and determining shelf life of product within the container based upon loss of the permeant through the container. The method includes the steps of (i) placing a sealed container containing a perishable product and a permeant within a sealed retention chamber, (ii) periodically measuring concentration of the permeant within the headspace of the retention chamber until a substantially steady state increase in permeant concentration within the headspace is sensed, and (iii) calculating a shelf life for the sealed container by dividing an amount of permeant loss, previously established as correlating to product expiration, by the sensed steady state increase in permeant concentration.

14 Claims, 2 Drawing Sheets

METHOD OF MEASURING THE TRANSMISSION RATE OF A PERMEANT THROUGH A CONTAINER AND DETERMINING SHELF LIFE OF A PACKAGED PRODUCT WITHIN THE CONTAINER

This application claims the benefit of U.S. Provisional Application No. 60/808,706, filed May 26, 2006.

BACKGROUND

Perishable products have a limited shelf life. Ascertaining the shelf life of perishable products is necessary to allow growers, suppliers and manufacturers to limit waste and ensure that product reaching consumers is fresh.

The shelf life of certain packaged products correlates well with loss of a given permeant through the package. One such packaged product is carbonated beverages, wherein the shelf life determining factor for the product is typically loss of carbonation.

While instruments and techniques are known and in use for measuring the transmission rate of a permeant through a container, a continuing need exists for a quick, accurate and cost effective method.

SUMMARY OF THE INVENTION

A first aspect of the invention is a method of measuring the transmission rate of a permeant through a container. The method includes the steps of (i) placing a sealed container containing permeant within a sealed retention chamber, and (ii) periodically measuring permeant concentration within the headspace of the retention chamber until a substantially steady state increase in permeant concentration within the headspace is sensed.

A second aspect of the invention is a method of determining shelf life of a packaged product within a sealed container based upon loss of a permeant through the container. The method includes the steps of (i) placing a sealed container containing a perishable product and a permeant within a sealed retention chamber, (ii) periodically measuring concentration of the permeant within the headspace of the retention chamber until a substantially steady state increase in permeant concentration within the headspace is sensed, and (iii) calculating a shelf life for the sealed container by dividing an amount of permeant loss, previously established as correlating to product expiration, by the sensed steady state increase in permeant concentration.

DETAILED DESCRIPTION OF AN EMBODIMENT OF THE INVENTION INCLUDING A BEST MODE

Nomenclature

10 Instrument
20 Housing
29 Retention Chamber
30 Cover Plate
41 Inlet Port
42 Outlet Port
50 Sensor
60 Pump
70 Collective Reference to Tubing
70a Length of Tubing Interconnecting the Outlet Port and the Sensor
70b Length of Tubing Interconnecting the Sensor and the Pump
70c Length of Tubing Interconnecting the Pump and the Inlet Orifice
80 Processor
85 Memory
90 User Interface Pad
91 ON/OFF Switch
92 Data Entry Device
100 Container
110 Product
120 Headspace
200 Battery

DEFINITIONS

As utilized herein, including the claims, the term "transmission rate" means the rate at which a permeant diffuses through a given container at standard pressure and temperature. The result is expressed as the volume or weight of permeant per day through the container.

As utilized herein, including the claims, the term "permeant" means any chemical substance which can diffuse through packaging material.

As utilized herein, including the claims, the term "headspace" means the volume remaining in the retention chamber after placement of a container within the chamber and the chamber is sealed.

As utilized herein, including the claims, the phrase "substantially steady state increase in permeant concentration" means rate of change in permeant concentration within a standard deviation of ±5%.

Structure

Figure 1:
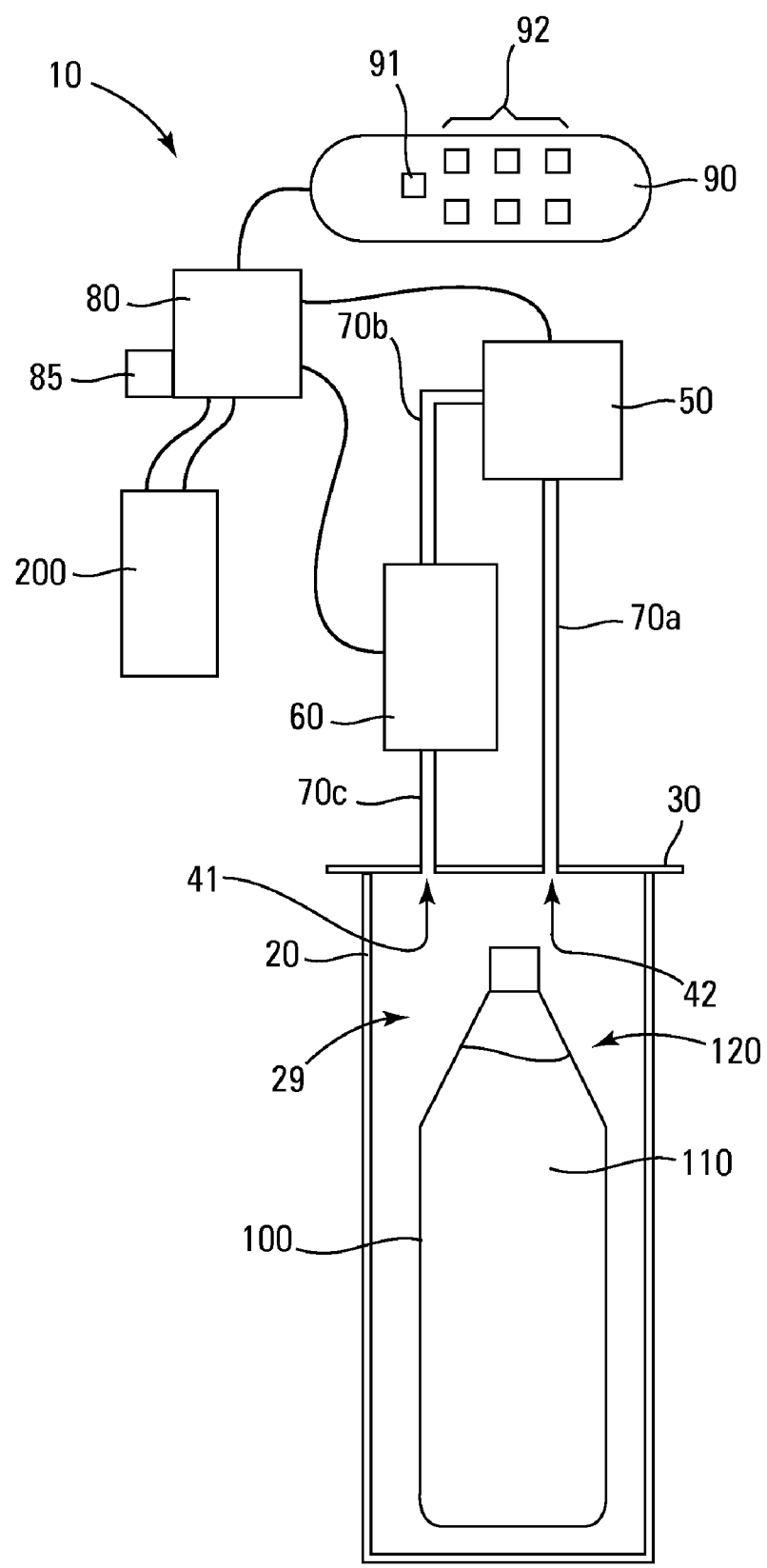
FIG. 1 is a schematic view of one embodiment of the invention.
Figure 2:
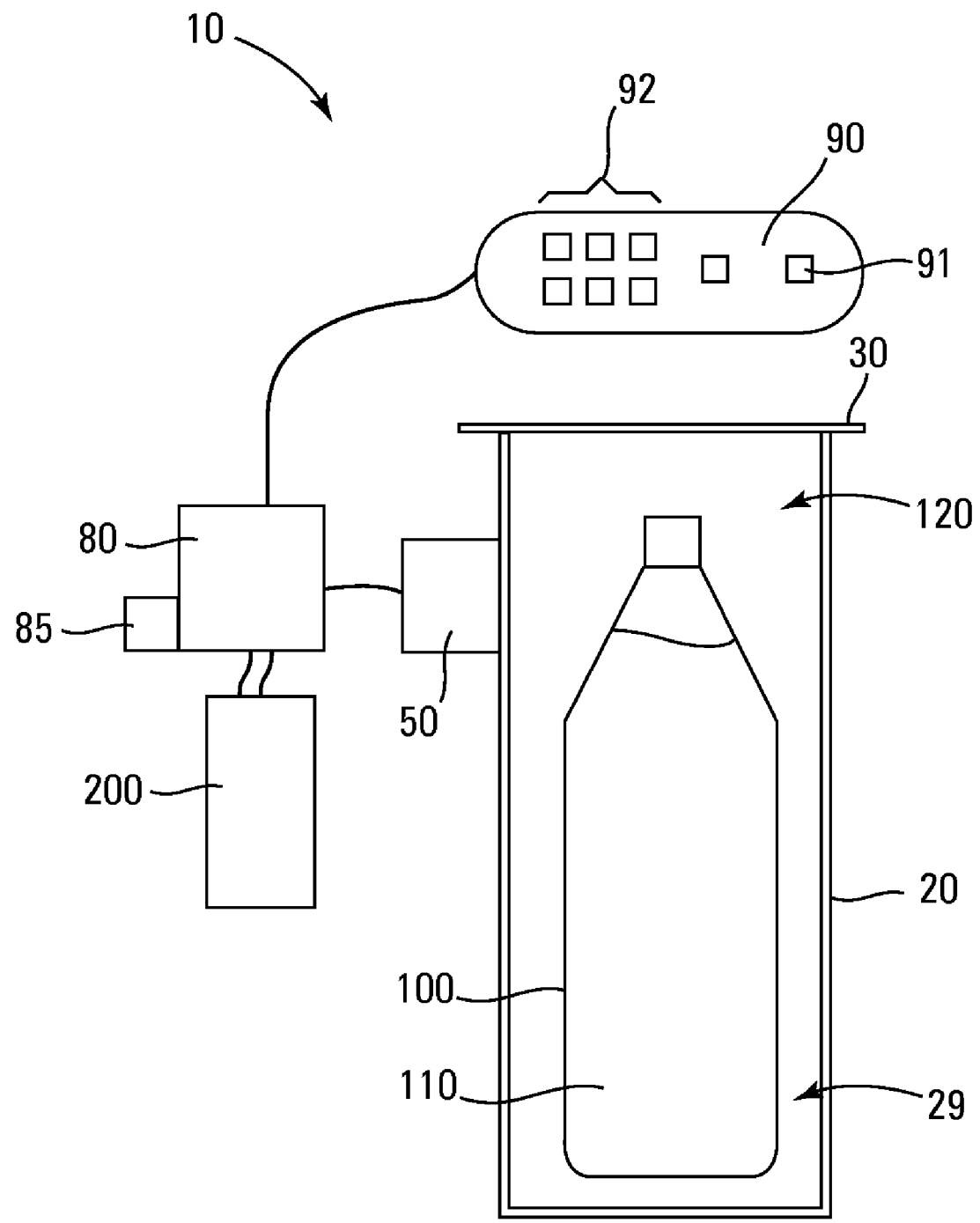
FIG. 2 is a schematic view of another embodiment of the invention.

As shown in FIGS. 1 and 2, a first embodiment of the invention is an instrument 10 for measuring the transmission rate of a permeant (not shown) through a container 100.

The instrument 10 can be effectively employed to measure the transmission rate of a wide variety of permeants through a wide variety of containers 100. Typical permeants of interest include $O_2$, water vapor and $CO_2$. Containers 100 may range from fairly rigid packaging such as thin-walled polyvinyl chloride tubes, through semi-flexible packaging such as wax-coated cartons and thin-walled polyethylene bottles, to flexible packaging such as bags made from polyethylene terephthalate (i.e., MYLAR®) or polyethylene films. A typical application of the instrument 10 is measurement of the transmission rate of $CO_2$ from a carbonated beverage through a plastic bottle. Without intending to be limited to this particular application, the balance of the disclosure shall reference this typical application.

Referring to FIG. 1, a first embodiment of the instrument 10 includes a housing 20, a cover plate 30, a sensor 50 for sensing permeant concentration, a pump 60, a processor 80, a user interface pad 90 and a battery 200. Appropriate tubing 70a, 70b, and 70c (hereinafter collectively referenced as tubing 70) sequentially interconnect an outlet port 42 in the cover plate 30, the gas sensor 50, the pump 60, and an inlet port 41 in the cover plate 30. Appropriate electrical leads (unnumbered) electrically connect the sensor 50, pump 60, processor 80, user interface pad 90 and battery 200.

Referring to FIG. 2, a second embodiment of the instrument 10 includes a housing 20, a cover plate 30, a sensor 50 for sensing permeant concentration, a processor 80, a user interface pad 90 and a battery 200. The sensor 50 extends through the housing 20 for direct contact with the headspace 120 in the retention chamber 29. Appropriate electrical leads (unnumbered) electrically connect the sensor 50, processor 80, user interface pad 90 and battery 200.

The housing 20 should be constructed from a material which is essentially impervious to and does not appreciably adsorb or transpire the permeant of interest. Most metals possess these desired properties. The housing 20 defines a retention chamber 29 and has an opening (unnumbered) for permitting the introduction and removal of containers 100 from the retention chamber 29. The cover plate 30 is configured and arranged to sealingly engage the opening through the housing 20 after a container 100 has been placed in the retention chamber 29. As with the housing 20, the cover plate 30 should be constructed from a material which is meaningfully impervious to and does not adsorb or transpire the permeant of interest.

The gas sensor 50 is effective for sensing and measuring the concentration of the permeant of interest—such as $CO_2$— within the headspace 120 of the retention chamber 29. Suitable sensors 50 for use in the instrument 10 include specifically, but not exclusively, commercially available infrared gas sensors.

Referring to FIG. 1, the gaseous content of the headspace 120 in the retention chamber 29 can be cycled past a remotely position gas sensor 50 through tubing 70 by pump 60. The pump 60 may be positioned upstream or downstream from the gas sensor 50. Substantially any type of pump 60 is suitable for use in the instrument 10, with selection dependent primarily upon choice of power source (i.e., battery or electrical power lines), desired level of portability (i.e., hand-held or desk-top), and size of the headspace 120. For most applications, a pump 40 with a maximum gas volumetric flow rate of about 250 to 1,000 $cm^3$/minute using standard consumer batteries (e.g., AAA, AA, A, C, D or 9-volt batteries) will be sufficient.

As with the housing 20 and cover plate 30, the tubing 70 should be constructed from a material which is essentially impervious to and does not appreciably adsorb or transpire the permeant of interest.

Referring to FIGS. 1 and 2, the sensor 50, and pump 60 (when employed) are operably interconnected to a microcontroller or processor 80 by appropriate leads (unnumbered) for controlling operation of the various components, and receiving and processing the data signals generated by the gas sensor 50. The processor 80 is connected to a suitable power source, such as a battery 200, by electrical leads (unnumbered). These components, along with the associated tubing 70, electrical leads (unnumbered) and a power source such as a battery 200, are preferably housed within a protective and cosmetic covering (not shown).

Referring generally to FIGS. 1 and 2, user interface components 90 are mounted on the covering (not shown) including (i) a power ON/OFF switch 91, (ii) a data entry device 92 (e.g., a keypad for entering alphanumeric characters or entering YES/NO responses, (iii) an LCD display (not shown), etc. The user interface components 90 are operably interconnected to the microcontroller or processor 60.

As shown in FIGS. 1 and 2, the microcontroller or processor 60 includes associated memory 65 for storing data values received from the gas sensor 50.

The microcontroller or processor 60 is programmed to (1) initiate testing upon receipt of a START command from a user, (2) periodically receive and record timed data values from the gas sensor 50 representing the concentration of a permeant of interest (e.g., $CO_2$), and (3) calculate the rate of change in sensed permeant concentration. Alternatively, the recorded data may be downloaded to a separate processing unit (not shown) (e.g., a desktop computer) for performance of step (3) upon completion of testing. The microcontroller or processor 60 can be programmed to continue this process until (i) an END command is received from a user, (ii) a predefined testing period is reached (e.g., 3 hours), (iii) a programmed definition of steady state increase in permeant concentration is achieved (e.g., upon receipt of data values over a thirty minute span producing the same calculated change in permeant concentration within a standard deviation of ±5%), or (iv) capacity of memory 85 has been reached. Regardless of the termination criteria employed, the criteria should be established to ensure that a substantially steady state increase in permeant concentration is achieved when the test is terminated.

The measured transmission rate of the permeant through the container 100 can be used to calculate a shelf life value for the container 100 by dividing an amount of permeant loss, previously established as correlating to expiration of product 110, by the measured transmission rate of the permeant through the container 100. This calculation can be conducted on board by the microcontroller or processor 60 or by a separate processing unit (not shown) after downloading of the recorded data.

The instrument 10 may be constructed as a portable or desktop unit.

EXAMPLES

GLOSSARY

| TERM | ACRONYM | DESCRIPTION |
| --- | --- | --- |
| Capture Volume | CV | Volume of the Retention Chamber |
| Bottle Volume (internal) | $BV_{INTERNAL}$ | Internal Volume of the Bottle |
| Bottle Volume (external) | $BV_{EXTERNAL}$ | Volume Occupied by the Bottle |
| Headspace Volume | HV | Capture Volume—Bottle Volume (external) |
| Bottle $CO_2$ Gas Volume (initial) | $BGV_{INITIAL}$ | Gas Volume Inside Bottle Under Pressure @ Commencement of Testing/Absolute Volume Inside Bottle |
| Bottle $CO_2$ Gas Volume (expiration) | $BGV_{EXPIRATION}$ | Gas Volume Inside Bottle @ Expiration of Product in Bottle/Absolute Volume Inside Bottle |

-continued

GLOSSARY

| TERM | ACRONYM | DESCRIPTION |
| --- | --- | --- |
| Overall Change in Bottle $CO_2$ Content to Expiration | $\Delta CO_{2\ BOTTLE}$ | $CO_2$ Volume at Commencement of Testing - $CO_2$ Volume at Expiration of Product in Bottle |
| Change in Headspace $CO_2$ Concentration Through Test Period | $\Delta CO_{2\ HEADSPACE}$ | $CO_2$ % at the end of the testing period—$CO_2$ % at the beginning of the testing period |
| Test Period | t | Duration of Test |
| Transmission Rate | TR | Rate of Transmission of $CO_2$ through a Barrier |

Example 1

The shelf life of a bottle of a carbonated beverage described in Table One, conditioned at room temperature and pressure for exactly five days prior to testing to permit the diffusion of $CO_2$ through the bottle to reach equilibrium, is determined using an instrument of the present invention having a capture volume of 3,535 cm$^3$

TABLE ONE

Bottle Parameters

| | |
| --- | --- |
| Bottle Temperature | 23° C. |
| Bottle Volume (internal) | 2,000 cm$^3$ |
| Bottle Volume (external) | 2,100 cm$^3$ |
| Bottle $CO_2$ Gas Volume (initial) | 4.0 |
| Bottle $CO_2$ Gas Volume (expiration) | 3.6 |

The Bottle $CO_2$ Gas Volume (initial) may be ascertained (i) immediately after the carbonated beverage is sealed within the bottle, (ii) at a time when the diffusion of $CO_2$ through the bottle is likely to have reached equilibrium, or (iii) upon commencement of testing. The bottle is sealed within the retention chamber of the instrument and the concentration of $CO_2$ within the headspace of the retention chamber is measured every two seconds for 3 hours (0.125 days). The difference between the concentration of $CO_2$ within the headspace of the retention chamber at the beginning of the testing period and at the end of the three hour testing period ($\Delta CO_{2\ HEADSPACE}$) is measured at 0.15%.

The transmission rate of $CO_2$ through the container is calculated as set forth below.

$$TR = (HV)(\Delta CO_{2\ HEADSPACE})/(100)(t)$$

wherein:

HV=Capture Volume−Bottle Volume (external)=3,535 cm$^3$−2,100 cm$^3$=1,435 cm$^3$ $\Delta CO_{2\ HEADSPACE}$=0.15%

T=0.125 days

∴TR=(1,435 cm$^3$)(0.15)/(100)(0.125 days)=17.22 cm$^3$/day

The simple shelf life of the carbonated beverage in the container, calculated without consideration of any decrease in TR over the shelf life resulting from a loss of pressure in the container, is calculated as set forth below.

Shelf Life (simple)=($\Delta CO_{2\ BOTTLE}$)/TR wherein:

$\Delta CO_{2\ BOTTLE}$=$CO_2$ Volume in Bottle at Commencement of Testing−$CO_2$ Volume in Bottle at Product Expiration wherein:

$CO_2$ Volume in Bottle at Commencement of Testing=(Bottle Volume (internal))(Bottle Gas Gas Volume (initial))=(2,000 cm$^3$)(4)=8,000 cm$^3$ -and- $CO_2$ Volume in Bottle at Expiration of Product=(Bottle Volume (internal))(Bottle Gas Gas Volume (expiration))=(2,000 cm$^3$)(3.6)=7,200 cm$^3$ ∴$\Delta CO_{2\ BOTTLE}$=8,000 cm$^3$−7,200 cm$^3$=800 cm$^3$ Shelf Life (simple)=800 cm$^3$/17.22 cm$^3$/day=46.45 days True shelf life of the product, based upon the calculated simple shelf life, is 51.45 days, ascertained by simply adding the five days during which the bottle was conditioned to the calculated simple shelf life.

A more accurate shelf life for the carbonated beverage in the container, one which factors in the decreasing TR over the shelf life of the product resulting from a loss of pressure in the bottle, can be calculated as set forth below.

Shelf Life=Log(% Total $CO_2$ Loss)/Log(% Daily $CO_2$ Loss)

wherein:

% Total $CO_2$ Loss=$CO_2$ Volume at Expiration of Product/$CO_2$ Volume at Commencement of Testing wherein:

$CO_2$ Volume at Expiration of Product=(Bottle Volume (internal))(Bottle Gas Volume (expiration))=(2,000 cm$^3$)(3.6)=7,200 cm$^3$ -and- $CO_2$ Volume at Commencement of Testing=(Bottle Volume (internal))(Bottle Gas Volume (initial))=(2,000 cm$^3$)(4)=8,000 cm$^3$ ∴% Total $CO_2$ Loss=7,200 cm$^3$/8,000 cm$^3$=0.900%

-and-

% Daily $CO_2$ Loss=(($CO_2$ Volume at Commencement of Testing)−(TR)(1 day))/($CO_2$ Volume at Commencement of Testing)=8,000 cm³−(17.22 cm³/day)(1 day)/8,000 cm³=0.99784

∴ Shelf Life=Log(0.90000)/Log(0.99784)=−0.04576/−0.0009390=48.73 days

True shelf life of the product, based upon this calculated shelf life, is 53.73 days, again ascertained by simply adding the five days during which the bottle was conditioned to the calculated shelf life.

We claim:

1. A method of measuring transmission rate of a permeant through a container, comprising: (a) placing a sealed container containing a permeant within a sealed retention chamber, and (b) periodically measuring permeant concentration within the headspace of the retention chamber until a substantially steady state increase in permeant concentration within the headspace is sensed, from which the transmission rate of the permeant through the container is measured, wherein the retention chamber remains sealed until a substantially steady state increase in permeant concentration within the headspace is sensed.

2. The method of claim 1 further comprising the step of reporting the sensed substantially steady state increase in permeant concentration within the headspace as the transmission rate of the permeant through the container.

3. The method of claim 1 further comprising the step of delaying placement of the container within the sealed chamber after the container is sealed, for a period of time effective for allowing diffusion of permeant through the container to at least approach a substantially steady state.

4. The method of claim 1 wherein the permeant is $CO_2$.

5. The method of claim 4 wherein the container contains a carbonated beverage.

6. The method of claim 5 wherein the container is a plastic bottle.

7. A method of determining shelf life of a packaged product within a sealed container based upon loss of a permeant through the container, comprising: (a) placing a sealed container containing a perishable product and a permeant within a sealed retention chamber, (b) periodically measuring concentration of the permeant within the headspace of the retention chamber until a substantially steady state increase in permeant concentration within the headspace is sensed, and (c) calculating a shelf life for the sealed container by dividing an amount of permeant loss, previously established as correlating to product expiration, by the sensed steady state increase in permeant concentration.

8. The method of claim 7 wherein (a) the container contains a known amount of the permeant immediately after sealing the permeant within the container, and (b) the amount of permeant loss correlating to product expiration is established by subtracting an amount of the permeant in the container previously established as correlating to product expiration from the amount of permeant in the container immediately after sealing the permeant within the container.

9. The method of claim 7 wherein (a) the container contains a known amount of shelf life governing permeant once diffusion of the permeant through the container substantially reaches steady state, and (b) the amount of permeant loss correlating to product expiration is established by subtracting an amount of the permeant in the container previously established as correlating to product expiration from the amount of permeant in the container once diffusion of the permeant through the container substantially reaches steady state.

10. The method of claim 7 wherein (a) the container contains a known amount of permeant when the container is placed in the sealed retention chamber, and (b) the amount of permeant loss correlating to product expiration is established by subtracting an amount of the permeant in the container previously established as correlating to product expiration from the amount of permeant in the container when the container is placed in the sealed retention chamber.

11. The method of claim 7 wherein a true shelf life is determined by adding the age of the sealed container prior to placing the container within the sealed retention chamber, and the calculated shelf life.

12. The method of claim 7 wherein the permeant is $CO_2$.

13. The method of claim 12 wherein the container contains a carbonated beverage.

14. The method of claim 13 wherein the container is a plastic bottle.

* * * * *